United States Patent [19]
Iwase et al.

[11] Patent Number: 6,117,897
[45] Date of Patent: Sep. 12, 2000

[54] 1/2 SULFATE OF A [(S)-1-[(S)-2-[(TRANS-4-AMINOCYCLOHEXYLMETHYL) CARBAMOYL]PYRROLIDINE-1-CARBONYL]-2-ISOPROPYLTHIO-2-METHYLPROPYL]CARBAMIC ACID PROPYL ESTER

[75] Inventors: Norimichi Iwase, Tokyo; Naoto Inakoshi; Koichi Sugawara, both of Yokohama; Jun Anabuki, Yokohama, all of Japan

[73] Assignee: Mitsubishi Chemical Corporation, Tokyo, Japan

[21] Appl. No.: 09/195,219

[22] Filed: Nov. 18, 1998

[30] Foreign Application Priority Data

Nov. 19, 1997 [JP] Japan ..................................... 9-318095

[51] Int. Cl.$^7$ .................................................. A01N 43/36
[52] U.S. Cl. ............................................. 514/423; 548/540
[58] Field of Search .............................. 514/423; 548/540

[56] References Cited

FOREIGN PATENT DOCUMENTS 669 317  8/1995  Japan .
846 682  6/1998  Japan .

*Primary Examiner*—Dwayne C. Jones
*Attorney, Agent, or Firm*—Oblon, Spivak, McClelland, Maier, & Neustadt, P.C.

[57] ABSTRACT

A 1/2 sulfate of a [(S)-1-[(S)-2-[(trans-4-aminocyclohexylmethyl) carbamoyl]pyrrolidine-1-carbonyl]-2-isopropylthio-2-methylpropyl]carbamic acid propyl ester represented by the following formula (I):

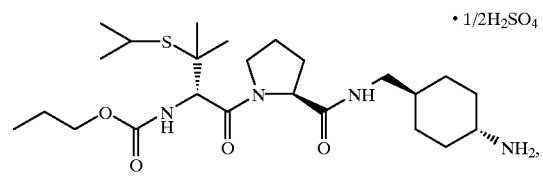

(I)

a hydrate or solvate thereof.

5 Claims, 3 Drawing Sheets

1/2 SULFATE OF A [(S) -1- [(S) -2- [(TRANS-4-AMINOCYCLOHEXYLMETHYL) CARBAMOYL]PYRROLIDINE-1-CARBONYL]- 2-ISOPROPYLTHIO-2-METHYLPROPYL]CARBAMIC ACID PROPYL ESTER

The present invention relates to a ½ sulfate of a [(S)-1-[(S)-2-[(trans-4-aminocyclohexylmethyl) carbamoyl]pyrrolidine-1-carbonyl]-2-isopropylthio-2 methylpropyll-carbamic acid propyl ester. This compound has a strong inhibitory activity against a protease, particularly against thrombin, and thus is useful as a therapeutic agent for e.g. thrombosis. Further, the same compound is able to be obtained as crystals which are physicochemically stable without hygroscopicity and thus is easy to produce by mass production and to formulate into various drug formulations.

The [(S)-1-[(S)-2-[(trans-4-aminocyclohexylmethyl) carbamoyl]pyrrolidine-1-carbonyl]-2-isopropylthio-2-methylpropyl]carbamic acid propyl ester is disclosed in the form of its hydrochloride in Example 1 of WO97/05108. This compound has a strong inhibitory activity against a protease, particularly against thrombin, and thus is useful as a therapeutic agent for e.g. thrombosis.

However, the hydrochloride of the [(S)-1-[(S)-2-[(trans-4-aminocyclohexylmethyl)carbamoyl]pyrrolidine-1-carbonyl]-2-isopropylthio-2-methylpropyllcarbamic acid propyl ester does not crystallize. Accordingly, in order to sufficiently improve the purity in its production, it is necessary to rely on column chromatography whereby a mass production is difficult.

Further, the hydrochloride of the [(S)-1-[(S)-2-[(trans-4-aminocyclohexylmethyl)carbamoyl]pyrrolidine-1-carbonyl]-2-isopropylthio-2-methylpropyl]carbamic acid propyl ester is highly hygroscopic, and it is rather difficult to produce stable tablets or the like from a composition containing such a hygroscopic hydrochloride.

The present inventors have conducted an extensive study to solve the above problems and as a result, have succeeded in accomplishing the present invention.

Namely, the present invention provides a ½ sulfate of a [(S)-1-[(S)-2-((trans-4-aminocyclohexylmethyl) carbamoyl]pyrrolidine-1-carbonyl]2-isopropylthio-2-methylpropyl]carbamic acid propyl ester represented by the following formula (I):

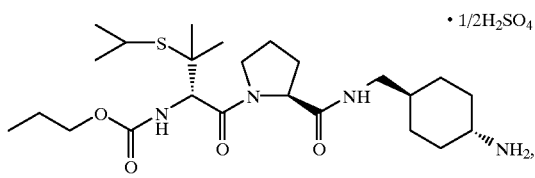

(I)
• 1/2H$_2$SO$_4$ a hydrate or solvate thereof.

As a preferred embodiment of the compound of the present invention, the ½ sulfate may be mentioned among the above compounds.

Further, as other embodiments, the present invention provides a pharmaceutical composition comprising the compound of the above formula (I) and a pharmaceutically acceptable carrier; a protease inhibitor comprising the compound of the above formula (I), as the active ingredient; and an anticoagulant comprising the compound of the above formula (I), as the active ingredient.

Figure 1:
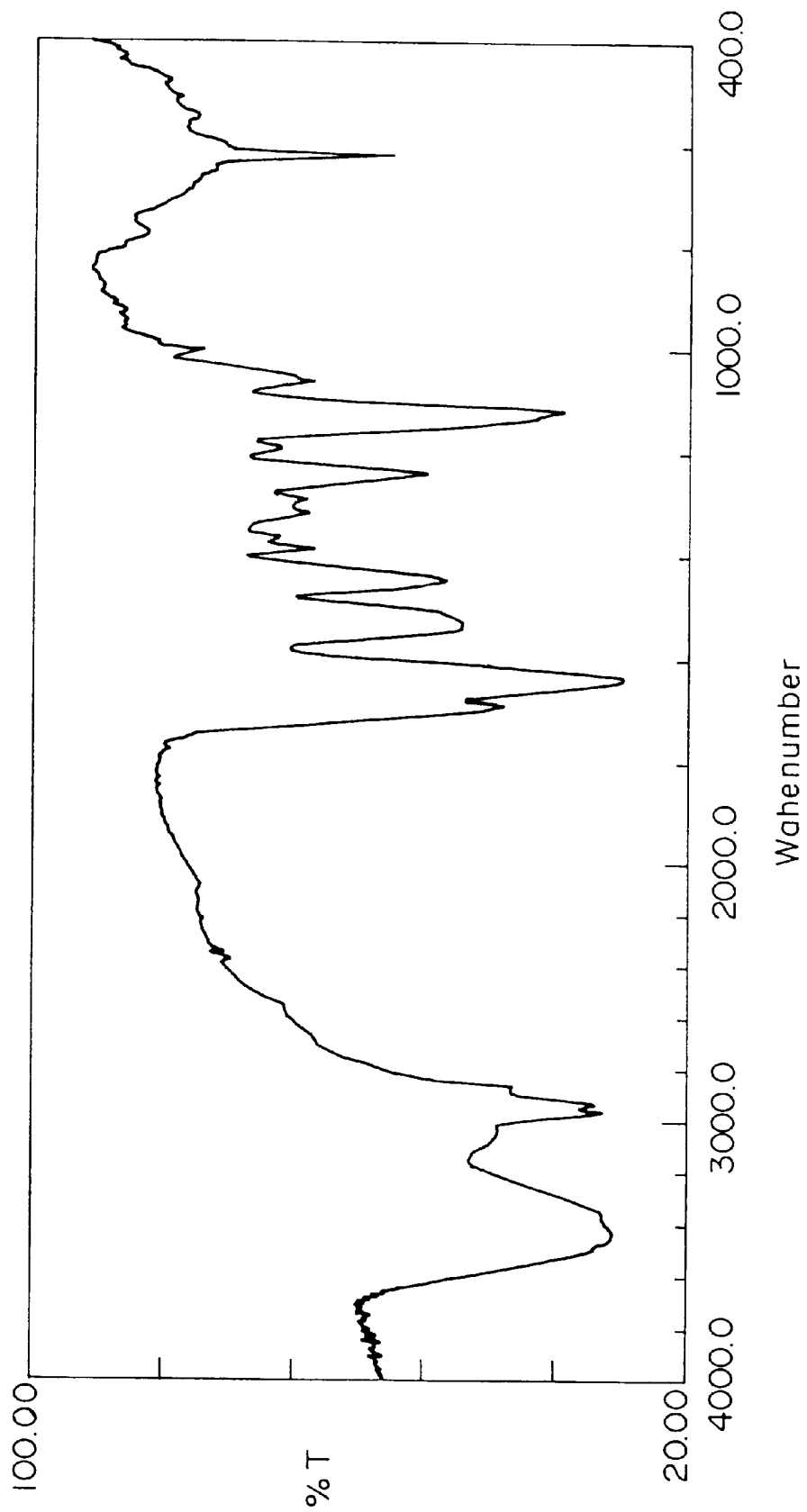
FIG. 1 is a graph showing the IR data of the compound of the present invention.

Now, the present invention will be described in detail with reference to the preferred embodiments.

The compound of the present invention is available in a plurality of crystal forms (they will be referred to A-form crystals, B-form crystals, . . . , respectively). The plurality of crystal forms may be used independently or in combination for medical compositions. However, it is preferred to use A-form crystals (the substance in Example 1 given hereinafter) which can be produced as a single type of crystals.

The compound of the above formula (I) may sometimes form a hydrate and may sometimes form a solvate with e.g. methanol, ethanol, isopropanol, acetone, ethyl acetate or methylene chloride. Such a hydrate and a solvate are included in the scope of the present invention.

When the compound of the present invention is to be used as a drug, it may be used by itself. However, it is usually preferred to use it in the form of a pharmaceutical composition comprising the compound of the present invention as the active ingredient and a pharmaceutically acceptable additive. The ratio of the active ingredient to the pharmaceutically acceptable additive may vary, for example, within a range of from 1 wt % to 90 wt %. The pharmaceutical composition containing the compound of the present invention may be administered, for example, in the form of a composition for oral administration such as a granule, a parvule, a powder, a tablet, a hard capsule, a soft capsule, a syrup, an emulsion, a suspension or a liquid formulation, or may be administered intravenously, intramuscularly or subcutaneously in the form of an injection drug. Otherwise, it can be used as a suppository. Further, it may be in the form of a powder for injection, which may be formed into an injection drug at the time of use.

As the pharmaceutically acceptable additive, a pharmaceutically acceptable organic or inorganic, solid or liquid carrier or diluent, may be employed, which is suitable for oral, intestinal or parenteral administration. As an excipient to be used for preparation of a solid pharmaceutical composition, lactose, sucrose, starch, talc, cellulose, dextrin, kaolin or calcium carbonate may, for example, be employed. A liquid composition for oral administration, such as an emulsion, a syrup, a suspension or a liquid formulation, may contain an inert diluent which is commonly employed, such as water or a vegetable oil. Such a liquid composition may contain in addition to the inert diluent, an adjuvant such as a wetting agent, a suspension adjuvant, a sweetener, a flavor, a coloring agent or a preservative. The liquid composition may be put into a capsule made of an absorbable material such as gelatin. As a solvent or suspending agent to be used for a pharmaceutical composition for parenteral administration such as an injection or suppository, water, propylene glycol, polyethylene glycol, benzyl alcohol, ethyl oleate or lecithin, may, for example, be mentioned. As the base material to be used for the suppository, cacao butter, emulsified cacao butter, laurin or Witepsol may, for example, be mentioned. The pharmaceutical composition may be prepared by a conventional method.

The clinical dose is such that in the case of oral administration, a daily dose is usually from 0.01 to 1,000 mg, preferably from 10 to 1,000 mg, as the compound of the present invention for an adult. However, the dose is suitably adjusted depending upon the age, the diseased condition or the symptom. The above daily dose of the drug of the present invention may be administered once a day or dividedly twice or three times a day with proper intervals.

Further, in the case of an injection, a dose of from 0.001 to 100 mg may be continuously or intermittently administered, as the compound of the present invention for an adult.

Now, the present invention will be described in further detail with reference to Examples. However, it should be understood that the present invention is by no means restricted by such specific Examples.

NMR for the physical property values, represents a nuclear magnetic resonance spectrum, and the numeral is δ (delta) value which is commonly used to indicate a chemical shift, whereby the unit is ppm. As the internal standard, tetramethylsilane was employed. Further, the symbols following it are such that s means singlet, d doublet, t triplet, m multiplet and bs a broad absorption peak, and the numeral following it indicates the number of hydrogen atoms.

Further, IR represents an infrared absorption spectrum, and it was measured in the form of potassium bromide tablet. The numeral represents the wave number, and the unit is $cm^{-1}$. Only main absorption peaks were shown.

EXAMPLE 1

Preparation of bis[[(S)-1-[(S)-2-[(trans-4-aminocyclohexylmethyl)carbamoyl]pyrrolidine-1-carbonyl]-2-isopropylthio-2-methylpropyl]carbamic acid propyl ester] sulfate 1,200 ml of a 4N hydrogenchloride-ethyl acetate solution was added to 200 g of [(S)-1-[(S)-2-[(trans-4-t-butoxycarbonylaminocyclohexylmethyl) carbamoyl]-pyrrolidine-1-carbonyl]-2-isopropylthio-2-methylpropyl] carbamic acid propyl ester prepared by the method as disclosed in Example 1 of WO97/05108, followed by stirring at 0° C. for 1 hour. This solution was concentrated by a rotary evaporator, and to the obtained residue, 1,800 ml of diethyl ether was added, followed by stirring at room temperature. Twenty-four hours later, the solid was collected by filtration and dissolved in 1,000 ml of dichloromethane, and a solution having 25 g of potassium hydroxide dissolved in 400 ml of water, was added thereto. The organic layer was separated, and the aqueous layer was extracted twice with dichloromethane. Then, the organic layer was dried over anhydrous magnesium sulfate. A solution obtained by filtration was concentrated by a rotary evaporator and then dried under reduced pressure of about 5 mmHg at room temperature to obtain 164 g of [(S)-1-[(S)-2-[(trans-4-aminocyclohexylmethyl)carbamoyl]pyrrolidine-1-carbonyl]-2-isopropylthio-2-methylpropyl]carbamic acid propyl ester.

$^1$H-NMR(DMSO-d6): 0.86–1.14(m, 7H), 1.25(d, J=6.9Hz, 3H), 1.32(d, J=6.9 Hz, 3H), 1.40(s, 3H), 1.47(s, 3H), 1.62(m, 6H), 1.69(m, 2H), 1.88(m, 2H), 2.03(m, 2H), 2.40(m, 1), 2.61(m, 1H), 2.90–3.15(m, 3H), 3.75(m, 1H), 3.97(m, 1H), 4.04(m, 1H), 4.37(d, J=6.6Hz, 1H), 4.59(d, J=8.1Hz, 1H), 5.57(bs, 1H), 7.10(bs, 1H).

IR: 3347, 2967, 1690, 1638, 1528, 1447, 1242, 1061.

Then, 164 g of [(S)-1-[(S)-2-[(trans-4-aminocyclohexylmethyl)carbamoyl]pyrrolidine-1-carbonyl]-2-isopropylthio-2-methylpropyl]carbamic acid propyl ester was dissolved in 2,000 ml of ethanol, and a solution having 15.8 g of sulfuric acid dissolved in 80 ml of water, was dropwise added at a temperature of from 0 to 5° C. This solution was concentrated by a rotary evaporator and dried under about 5 mmHg at room temperature. To this solid, 600 ml of ethanol and 1,000 ml of hexane were added, followed by stirring at room temperature for 6 hours and then by filtration to obtain 146 g of the above-identified compound.

Melting point: 238–240° C.

Results of elemental analysis

Measured values: C 53.8, H 8.60, N 10.50, S 8.90

Theoretical values: C 54.0, H 8.59, N 10.49, S 9.01

$^1$H-NMR(DMSO-d6): 0.80–0.94(m, 5H), 1.10–1.32(m, 12H), 1.36(s, 3H), 1.55(m, 2H), 1.68(m, 2H), 1.78–2.06(m, 6H), 2.74(m, 1H), 2.86(m, 2H), 2.98(m, 1H), 3.71(m, 2H), 3.92–4.00(m, 2H), 4.22(d, J=7.9 Hz, 1H), 4.45(d, J=8.5 Hz, 1H), 7.36(d, J=8.5 Hz, 1H), 7.50(bs, 1H).

Figure 2:
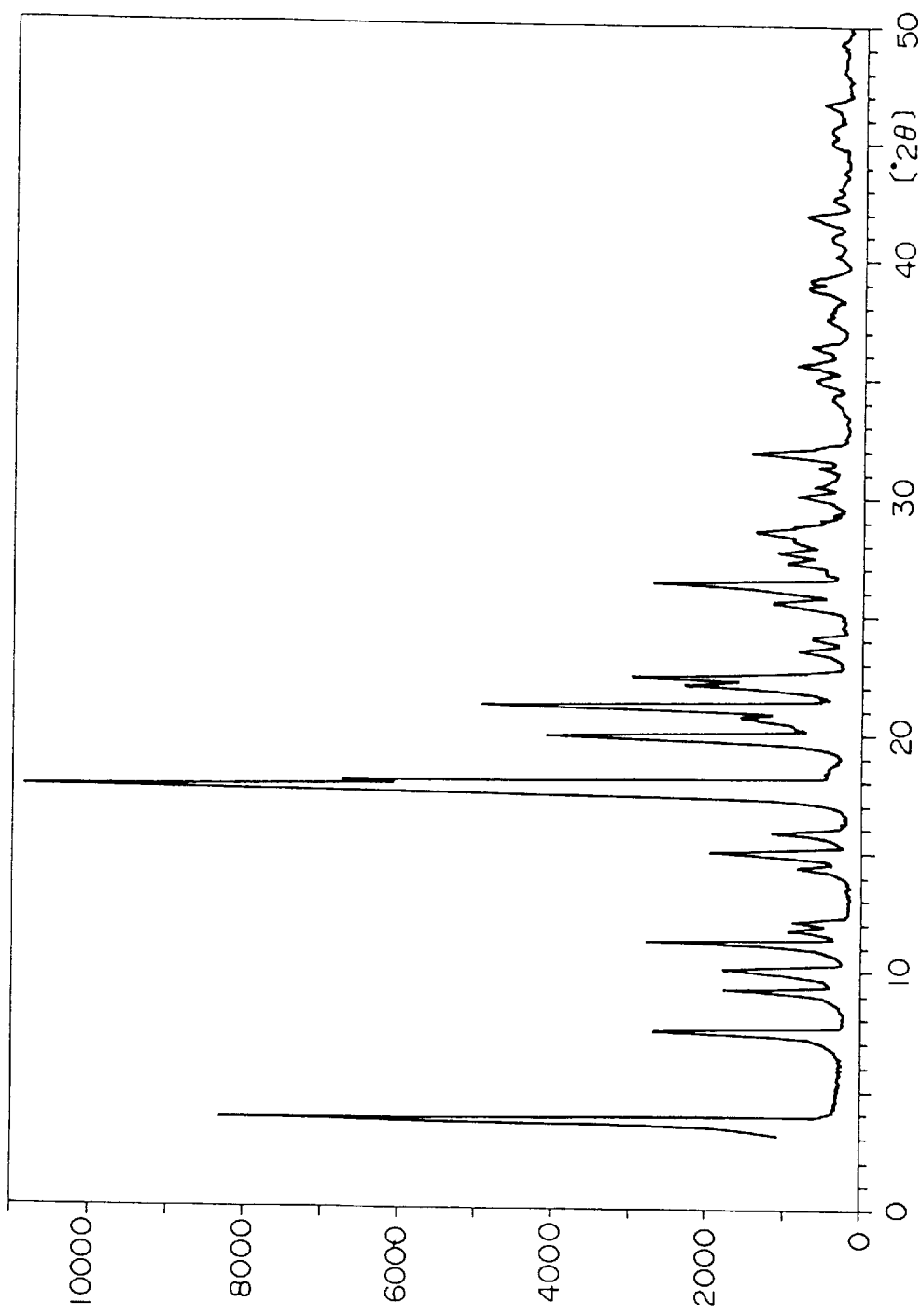
FIG. 2 is a graph showing the powder X-ray data of the compound of the present invention.

IR data and powder X-ray data are shown in FIGS. 1 and 2, respectively.

EXAMPLE 2

Preparation of bis[[(S)-1-[(S)-2-[(trans-4-aminocyclohexylmethyl)carbamoyl]pyrrolidine-1-carbonyl]-2-isopropylthio-2-methylpropyl]carbamic acid propyl ester] sulfate 10 g of [(S)-1-[(S)-2-(trans-4-tbutoxycarbonylaminocyclohexylmethylcarbamoyl) pyrrolidine 1-carbonyl]2-isopropylthio-2-methylpropyl] carbamic acid propyl ester] was dissolved in 73 ml of dichloromethane, and 10 ml of concentrated hydrochloric acid was added thereto, followed by stirring at room temperature for 4 hours. A solution having 6.6 g of sodium chloride and 5.8 g of sodium hydroxide dissolved in 66 ml of water, was added thereto, followed by stirring at room temperature for 1 hour. The organic layer was separated, and the aqueous layer was extracted once with dichloromethane. The organic layer was washed with water, dried over sodium sulfate and subjected to filtration, and the solution thereby obtained was concentrated by a rotary evaporator to about 30 ml. Then, 17.1 ml of IN sulfuric acid and 100 ml of isopropanol were added thereto, followed by filtration, and the obtained solution was concentrated to about 40 ml. Then, 110 ml of isopropanol was added thereto, and the mixture was concentrated to 40 ml. Further, this operation was repeated once. To the obtained solution, 110 ml of isopropanol was added, and the mixture was refluxed under heating for 2 hours and then cooled to room temperature, and it was further stirred for 2 hours. A solid was collected by filtration and dried under a reduced pressure of about 5 mmHg at 60° C. to obtain 8.3 g of the above-identified compound.

Melting point: 245–246° C. (decomposed)

Results of elemental analysis

Measured values: C 53.95, H 8.72, N 10.53, S 8.98

Figure 3:
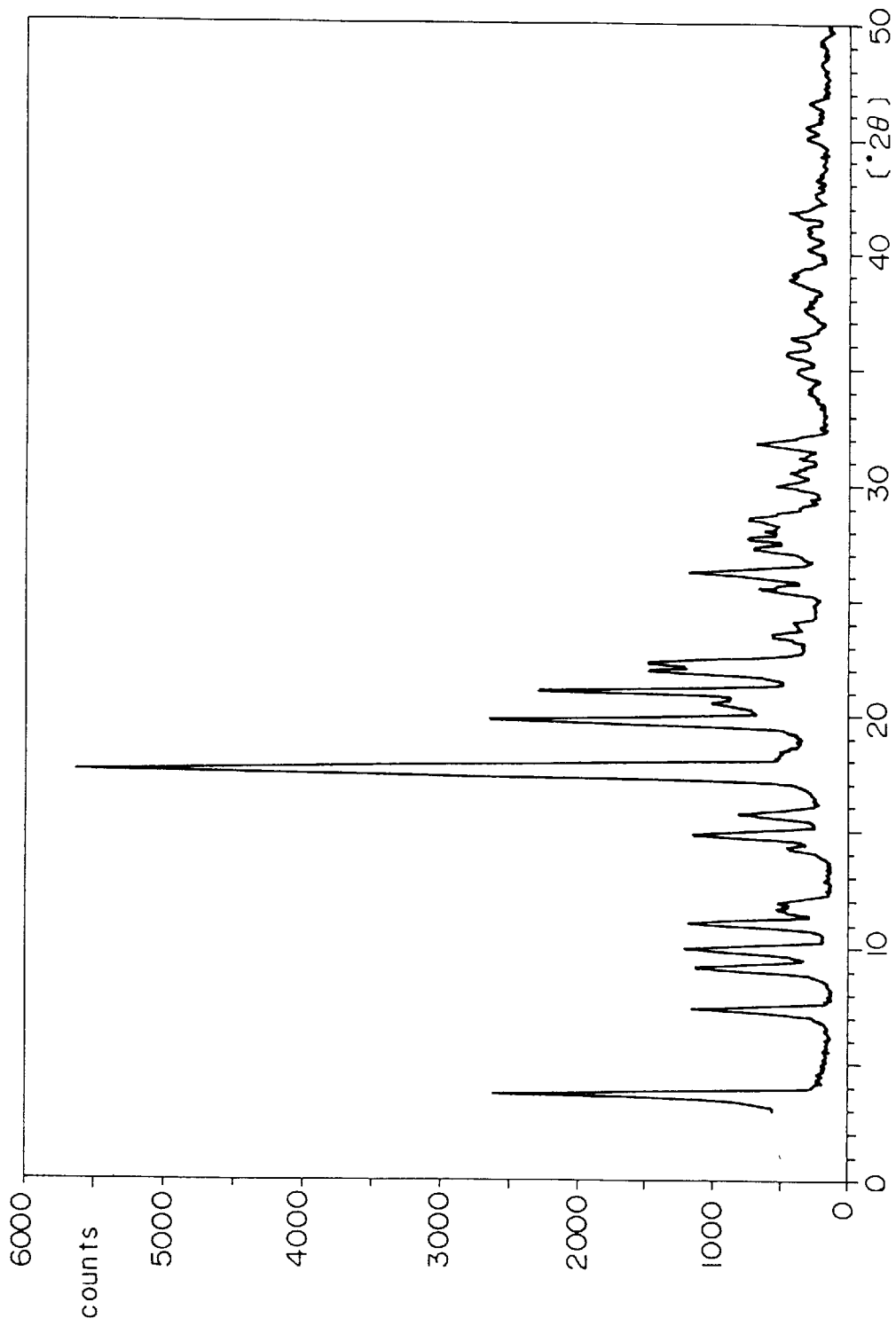
FIG. 3 is a graph showing the powder X-ray data of the compound of the present invention.

Theoretical values: C 54.0, H 8.59, N 10.49, S 9.01 Powder X-ray data are shown in FIG. 3.

Test Example 1

Hygroscopicity Test

The hygroscopicity data were evaluated in such a manner that a container containing a test sample in a desiccator containing a saturated sodium acetate aqueous solution, was left to stand at room temperature, whereby the change in the state and the weight change of the test sample were observed.

The compound of the present invention obtained in Example 1 was left to stand for 3 days under the above conditions, whereby the state of the compound remained to be constant as a white powder, and the weight change was ±0%. Then, it was left to stand for further 4 days under the above conditions, whereby the state did not change as a white powder, and the weight change was ±0%.

The same hygroscopicity test was carried out with respect to the substances obtained in Example 2 and the following Reference Example 3, 4, 12 and 13. The results are shown in Table 1.

TABLE 1

Crystallization and hygroscopicity test

| | Form of salt | Solvent | Results of hygroscopicity test (*3) | |
|---|---|---|---|---|
| | | | 3 days later | 7 days later |
| Example 1 | 1/2 $H_2SO_4$ salt | EtOH-hexane | White powder (±0%) | White powder (±0%) |
| Example 2 | 1/2 $H_2SO_4$ salt | i-PrOH | White powder (±0%) | White powder (±0%) |
| Test Example 3 | HCl salt | THF-hexane (*2) | Colorless oil (+9%) | — |
| Test Example 4 | HCl salt | $CH_2Cl_2$-hexane | Colorless oil (+9%) | — |
| Test Example 12 | TsOH salt (*1) | THF-hexane (*2) | Colorless oil (+9%) | — |
| Test Example 13 | TsOH salt (*1) | $CH_2Cl_2$-hexane | Colorless oil (+14%) | — |

*1: TsOH salt = p-toluenesulfonate
*2: THF = tetrahydrofuran
*3: The state and the weight change are indicated.

Reference Example 1

Preparation of [(S)-1-[(S)-2-[(trans-4-aminocyclohexylmethyl)carbamoyl]pyrrolidine-1-carbonyl]-2-isopropylthio-2-methylpropyl]carbamic acid propyl ester hydrochloride 0.49 g of [(S)-1-[(S)-2-[(trans-4-aminocyclohexylmethyl)carbamoyl]pyrrolidine-1-carbonyl]2-isopropylthio-2-methylpropyl]carbamic acid propyl ester obtained in Example 1was dissolved in 5 ml of ethanol, and 1.0 ml of 1N hydrochloric acid was added thereto, followed by stirring at room temperature for 30 minutes. The solvent was distilled off under reduced pressure, and then, 5 ml of toluene was added thereto and then distilled under reduced pressure. The residue was dried under a reduced pressure of about 10 mmHg at room temperature to obtain 0.54 g of a white amorphous substance.

Test Example 2
Crystallization of Hydrochloride (1)

0.20 g of the compound obtained in Reference Example 1 was dissolved in 1 ml of ethanol, and 3 ml of hexane was added thereto, followed by stirring at room temperature. However, one day later, no crystal was obtained.

Test Example 3
Crystallization of Hydrochloride (2)

0.20 g of the compound obtained in Reference Example 1 was dissolved in 2 ml of tetrahydrofuran, and 1 ml of hexane was dropwise added thereto, whereupon the solution slightly turbidified and reached a saturated state. The solution was stirred at room temperature, and the precipitated substance was collected by filtration and dried under a reduced pressure of about 10 mmHg at 60° C. to obtain 0.19 g of a white powder.

Test Example 4
Crystallization of hydrochloride (3)

0.20 g of the compound obtained in Reference Example 1 was dissolved in 1 ml of methylene chloride, and 2 ml of hexane was dropwise added thereto, whereupon the solution slightly turbidified and reached a saturated state. The solution was stirred at room temperature, and the precipitated substance was collected by filtration and dried under a reduced pressure of about 10 mmHg at 60° C. to obtain 0.15 g of a white powder.

Reference Example 2

Preparation of [(S)-1-[(S)-2-[(trans-4-aminocyclohexylmethyl)carbamoyl]pyrrolidine-1-carbonyl]-2-isopropylthio-2-methylpropyl]carbamic acid propyl ester nitrate 0.49 g of [(S)-1-[(S)-2-[(trans-4-aminocyclohexylmethyl)carbamoyl]pyrrolidine-1-carbonyl]-2-isopropylthio-2-methylpropyl]carbamic acid propyl ester obtained in Example 1 was dissolved in 5 ml of ethanol, and 1.0 ml of 1N nitric acid was added thereto, followed by stirring at room temperature for 30 minutes. The solvent was distilled off under reduced pressure, and then, 5 ml of toluene was added thereto and then distilled off under reduced pressure. The residue was dried under a reduced pressure of about 10 mmHg at room temperature to obtain 0.56 g of a white amorphous substance.

$^1$H-NMR(DMSO-d6): 0.82–1.04(m, 5H), 1.10–1.35(m, 12H), 1.37(s, 3H), 1.57(m, 2H), 1.70(m, 2H), 1.78–2.10(m, 6H), 2.74 (m, 1H), 2.90(m, 2H), 3.00 (m, 1H), 3.77(m, 2H), 3.90(m, 1H), 3.95(m, 1H), 4.22(d, J=6.8 Hz, 1H), 4.45(d, J=8.4 Hz, 1H), 7.33(d, J=8.3 Hz, 1H), 7.57(bs, 1H).

IR: 3347, 2967, 1692, 1640, 1541, 1439, 1383, 1242, 1061.

Test Example 5
Crystallization of Nitrate (1)

0.20 g of the compound obtained in Reference Example 2 was dissolved in 1 ml of ethanol, and 3 ml of hexane was added thereto, followed by stirring at room temperature. However, one day later, no crystal was obtained.

Test Example 6
Crystallization of Nitrate (2)

0.20 g of the compound obtained in Reference Example 2 was dissolved in 1 ml of methylene chloride, and 1.5 ml of hexane was dropwise added thereto, whereupon the solution slightly turbidified and reached a saturated state. This solution was stirred at room temperature for 1 day, whereby an oily substance was separated, and no crystal was obtained.

Reference Example 3

Preparation of [(S)-1-[(S)-2-[(trans-4-aminocyclohexvlmethyl)carbamoyl]pyrrolidine-1-carbonyl]-2-isooropylthio-2-methylpropyl]carbamic acid propyl ester acetate 0.49 g of [(S)-1-[(S)-2-[(trans-4-aminocyclohexylmethyl) carbamoyl]pyrrolidine-1-carbonyl]2-isopropylthio-2-methylpropyl]carbamic acid propyl ester obtained in Example 1 was dissolved in 5 ml of methylene chloride, and 63 mg of acetic acid was added thereto, followed by stirring at room temperature for 30 minutes. The solvent was distilled off under reduced pressure, and the residue was dried under a reduced pressure of about 10 mmHg at room temperature to obtain 0.55 g of a white amorphous substance.

$^1$H-NMR(DMSO-d6): 0.79–0.96(m, 5H), 1.02–1.32(m, 12H), 1.37(s, 3H), 1.50–1.72(m, 4H), 1.76(s, 2H), 1.78–2.08 (m, 6H), 2.62(m, 1H), 2.85(m, 2H), 3.00(m, 1H), 3.72(m, 2H), 3.84–4.01(m, 2H), 4.22(d, J=6.8Hz, 1H), 4.45(d, J=8.4 Hz, 1H), 7.36(d, J=8.3 Hz, 1H), 7.55(bs, 1H).

IR: 3322, 2965, 1642, 1549, 1242, 1061.

Test Example 7

Crystallization of Acetate (1)

0.20 g of the compound obtained in Reference Example 3 was dissolved in 1 ml of ethanol, and 3 ml of hexane was added thereto, followed by stirring at room temperature. However, one day later, no crystal was obtained.

Test Example 3

Crystallization of Acetate (2)

0.20 g of the compound obtained in Reference Example 3 was dissolved in 1 ml of methylene chloride, and 2 ml of hexane was dropwise added thereto, whereupon the solution slightly turbidified and reached a saturated state. This solution was stirred at room temperature for 1 day, whereby an oily substance separated, and no crystal was obtained.

Reference Example 4

Preparation of [(S)-1-[(S)-2-[(trans-4-aminocyclohexylmethyl) carbamoyl]pyrrolidine-1-carbonyl]-2-isopropylthio-2-methylprop]carbamic acid propyl ester sulfate 0.49 g of [(S)-1-[(S)-2-[(trans-4-aminocyclohexylmethyl) carbamoyl]pyrrolidine-1-carbonyl]-2-isopropylthio-2-methylpropyl]carbamic acid propyl ester obtained in Example 1 was dissolved in 5 ml of ethanol, and 2 ml of 1N sulfuric acid was added thereto, followed by stirring at room temperature for 30 minutes. The solvent was distilled off under reduced pressure, and then 5 ml of toluene was added thereto, and then distilled under reduced pressure. The residue was dried under a reduced pressure of about 10 mmHg at room temperature to obtain 0.60 g of a white amorphous substance.

$^1$H-NMR(DMSO-d6): 0.84–1.04(m, 5H), 1.12–1.34(m, 12H), 1.38(s, 3H), 1.58(m, 2H), 1.70(m, 2H), 1.80–2.06(m, 6H), 2.89(m, 3H), 3.00(m, 1H), 3.77(m, 2H), 3.91(m, 1H), 3.96(m, 1H), 4.22(d, J=6.8 Hz, 1H), 4.45(d, J=8.4 Hz, 1H), 7.33(d, J=8.3 Hz, 1H), 7.60(bs, 1H), 7.72(bs, 3H).

IR: 3399, 2967, 1696, 1638, 1524, 1447, 1225, 1192, 1049, 889.

Test Example 9

Crystallization of Sulfate (1)

0.20 g of the compound obtained in Reference Example 4 was dissolved in 1 ml of ethanol, and 3 ml of hexane was added thereto, followed by stirring at room temperature. However, one day later, no crystal was obtained.

Test Example 10

Crystallization of Sulfate (2)

0.20 g of the sulfate obtained in Reference Example 4 was dissolved in 1 ml of methylene chloride, and 1.2 ml of hexane was dropwise added thereto, whereupon the solution slightly turbidified and reached a saturated state. This solution was stirred at room temperature for 1 day, whereby an oily substance separated and no crystal was obtained.

Reference Example 5

Preparation of [(S)-1-[(S)-2-[(trans-4-aminocyclohexylmethyl)carbamoyl]pyrrolidine-1-carbonyl]2-isoprooylthio-2-methylpropyl]carbamic acid propyl ester p-toluenesulfonate 0.49 g of [(S)-1-[(S)-2-[(trans-4-aminocyclohexylmethyl) carbamoyl]pyrrolidine-1-carbonyl]-2-isopropylthio-2-methylpropyl]carbamic acid propyl ester obtained in Example 1 was dissolved in 5 ml of methylene chloride, and 0.19 ml of p-toluenesulfonic acid monohydrate was added thereto, followed by stirring at room temperature for 30 minutes. The solvent was distilled off under reduced pressure, and the residue was dried under a reduced pressure of about 10 mmHg at room temperature to obtain 0.66 g of a white amorphous substance.

$^1$H-NMR(DMSO-d6): 0.82–1.04(m, 5H), 1.10–1.34(m, 12H), 1.36(s, 3H), 1.57(m, 2H), 1.70(m, 2H), 1.78–2.10(m, 6H), 2.29(s, 3H), 2.89(m, 3H), 3.00(m, 1H), 3.77(m, 2H), 3.90(m, 1H), 3.96(m, 1H), 4.22(d, J=6.8 Hz, 1H), 4.45(d, J=8.4Hz, 1H), 7.12(d, J=8.0 Hz, 2H), 7.33(d, J=8.3 Hz, 1H), 7.48(d, J=8.4 Hz, 2H), 7.60(bs, 1H), 7.73(bs, 3H).

IR: 3445, 3347, 3061, 2967, 1670, 1640, 1535, 1449, 1215, 1188, 1125, 1036, 1011, 685.

Test Example 11

Crystallization of p-toluenesulfonate (1)

0.20 g of the p-toluenesulfonate obtained in Reference Example 5 was dissolved in 1 ml of ethanol, and 3 ml of hexane was added thereto, followed by stirring at room temperature. However, one day later, no crystal was obtained.

Test Example 12

Crystallization of p-toluenesulfonate (2)

0.20 g of the compound obtained in Reference Example 5 was dissolved in 1 ml of tetrahydrofuran, and 1 ml of hexane was dropwise added thereto, whereupon the solution slightly turbidified and reached a saturated state. The solution was stirred at room temperature, and the precipitated substance was collected by filtration and dried under a reduced pressure of about 10 mmHg at 55° C. to obtain 0.18 g of a white powder.

Test Example 13
Crystallization of p-toluenesulfonate (3)

0.20 g of the compound obtained in Reference Example 5 was dissolved in 1 ml of methylene chloride, and 1.4 ml of hexane was dropwise added thereto, whereupon the solution slightly turbidified and reached a saturated state. The solution was stirred at room temperature, and the precipitated substance was collected by filtration and dried under a reduced pressure of about 10 mmHg at 55° C. to obtain 0.16 g of a white powder.

Test Example 14
Measurement of the Anti-Thrombin Activity i) Method for measuring suppression of hydrolysis of a synthesized substrate (S-2238)

S-2238 (Kabi Co.) was dissolved by a trishydrochloride buffer solution (pH 8.3) to obtain a 0.4M trishydrochloride solution of S-2238 having a concentration of 80 µM. To 175 µl thereof, 515 µl of an aqueous solution of the compound of the present invention was added, followed by incubation at 37° C. for 1 minute. Then, 10 µl of a 4.4 units/ml solution of bovine thrombin (Mochida Co.) was added thereto. The reaction rate of the hydrolysis of the substrate was obtained by measuring the change in absorbance of 405 nm at 37° C.

The concentration of the inhibitor showing an absorbance corresponding to ½ of the absorbance where no inhibitor (the compound of the present invention) was incorporated, was obtained as $I_{50}$ (µM).

ii) Method for measuring suppression of coagulation of rat blood plasma

The compound of the present invention was dissolved in water or in a physiological sodium chloride aqueous solution to bring the total volume to 0.1 ml, and 0.1 ml of rat blood plasma was added thereto, followed by incubation at 37° C. for 30 seconds. 0.1 ml of a 8 units/ml solution of bovine thrombin (Mochida Co.) was added thereto, whereupon the coagulation time at 37° C. was measured. The concentration of the inhibitor prolonging the coagulation time twice the coagulation where no inhibitor (the compound of the present invention) was incorporated, was obtained as $I_{50}$ (mM).

iii) Method for measuring the anti-thrombin activity in the blood plasma at the time of oral administration to a rat To a rat fasted overnight, 30 mg/kg of the compound of the present invention was orally administered by means of an oral probe in the form of an aqueous solution or suspension.

One hour later and three hours later, 2 ml of blood was collected from the abdominal vena cava, and the antithrombin activity in the plasma was measured by the method of the above ii). As compared with the blood of a rat having no inhibitor (the compound of the present invention) administered, the effect for prolonging the coagulation time was represented by a numerical value against a control being 1, as the thrombin time prolongation.

Test Example 3
Measurement of the Anti-Trypsin Activity i) Method for measuring suppression of hydrolysis of a synthesized substrate (S-2222)

S-2222 (Kabi Co.) was dissolved with a trishydrochloride buffer solution (pH 8.3) to obtain a 0.4M trishydrochloride solution of S-2222 having a concentration of 400 mM. To 175 µl thereof, 515 µl of an aqueous solution of the compound of the present invention was added, followed by incubation at 37° C. for 1 minute. Then, 10 µl of a 1 or 2 mg/ml solution of bovine trypsin (Sigma Co.) was added thereto. The reaction rate of hydrolysis of the substrate was determined by measuring the change in absorbance of 405 nm at 37° C.

The concentration of the inhibitor showing an absorbance corresponding to ½ of the absorbance where no inhibitor (the compound of the present invention) was incorporated, was obtained as $I_{50}$ (µM).

The results of the foregoing are shown in Table 2.

TABLE 2

| Example No. | Anti-thrombin activity $I_{50}$ (µm) | | Anti-trypsin activity $I_{50}$ (µm) | Thrombin time prolongation by oral administration | |
|---|---|---|---|---|---|
| | Synthesized substrate method | Rat plasma method | | 1 hr | 3 hrs |
| 1 | 0.013 | 0.045 | 41 | 2.99 | 5.92 |

What is claimed is:

1. A 1/2 sulfate of a [(S)-1-[(S)-2-[(trans-4-aminocyclohexylmethyl)carbamoyl]pyrrolidine-1-carbonyl]-2-isopropylthio-2-methylpropyl]carbamic acid propyl ester represented by the following formula (I):

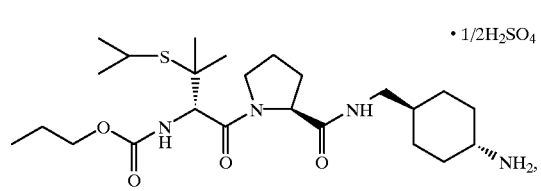

(I)

a hydrate or solvate thereof.

2. A 1/2 sulfate of a [(S)-1-[(S)-2-[(trans-4-aminocyclohexylmethyl) carbamoyl]pyrrolidine-1-carbonyl]-2-isopropylthio-2-methylpropyl]carbamic acid propyl ester.

3. A pharmaceutical composition comprising the compound as defined in claim 1 and a pharmaceutically acceptable carrier.

4. A method of inhibiting protease activity which comprises administering to a subject in need thereof, a compound as defined in claim 1, in an amount effect to inhibit protease activity.

5. A method of inhibiting clotting of blood which comprises administering to a subject in need thereof, a compound as defined in claim 1, in an amount effective to inhibit blood clotting.

* * * * *